(12) United States Patent
Jung et al.

(10) Patent No.: US 7,902,122 B2
(45) Date of Patent: Mar. 8, 2011

(54) METHOD FOR DETECTING TARGET BIOLOGICAL MATERIAL USING DNA BARCODES

(75) Inventors: Sang Don Jung, Daejeon (KR); Myung Ae Chung, Daejeon (KR); Hyo Bong Hong, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 657 days.

(21) Appl. No.: 11/758,735

(22) Filed: Jun. 6, 2007

(65) Prior Publication Data

US 2009/0005255 A1    Jan. 1, 2009

(30) Foreign Application Priority Data

Dec. 6, 2006    (KR) .................. 10-2006-0123353

(51) Int. Cl.
*C40B 70/00*    (2006.01)
(52) U.S. Cl. ................... 506/41; 435/6; 506/4; 536/23.1
(58) Field of Classification Search .................. None
See application file for complete search history.

(56) References Cited

U.S. PATENT DOCUMENTS

| | | | |
|---|---|---|---|
| 5,512,439 A | 4/1996 | Hornes et al. | |
| 6,013,531 A | 1/2000 | Wang et al. | |
| 6,133,436 A | 10/2000 | Koster et al. | |
| 6,355,431 B1 | 3/2002 | Chee et al. | |
| 6,514,688 B2 | 2/2003 | Muller-Schulte | |
| 6,875,568 B2 | 4/2005 | Nisson et al. | |
| 2004/0009614 A1 | 1/2004 | Ahn et al. | |
| 2005/0037397 A1* | 2/2005 | Mirkin et al. | 435/6 |
| 2010/0129793 A1* | 5/2010 | Mirkin | 435/6 |

FOREIGN PATENT DOCUMENTS

KR    1020050044559 A    5/2005

OTHER PUBLICATIONS

Yeung, S.W., et al. (2005). "Manipulation and extraction of genomic DNA from cell lysate by functionalized magnetic particles for lab on a chip applications." *Science Direct—Elsevier—Biosensors and Bioelectronics* 21. pp. 989-997.
Nam, J., et al. (2003). "Nanoparticle-Based Bio-Bar Codes for the Ultrasensitive Detection of Proteins." Science. vol. 301. pp. 1884-1886.

* cited by examiner

*Primary Examiner* — Amber D. Steele
*Assistant Examiner* — Christopher M Gross
(74) *Attorney, Agent, or Firm* — Ladas & Parry LLP

(57) ABSTRACT

A method for detecting a target biological material using DNA barcodes is provided. The method is for detecting a target biological material (e.g., DNA) by using DNA barcodes by which a trace amount of target biological material can be detected in a rapid and economic manner without performing polymerase chain reaction (PCR). The method is characterized by the use of magnetic particles and polymer particles coated with DNA barcodes to sense a trace amount of a biological material (e.g., DNA).

12 Claims, 13 Drawing Sheets

SEQUENCE LISTING

<160> NUMBER OF SEQ ID NOS: 12

<210> SEQ ID NO 1
<211> LENGTH: 13
<212> TYPE: DNA
<213> ORGANISM: Unknown
<220> FEATURE:
<223> OTHER INFORMATION: exemplary sequence used to illustrate invention

```
<220> FEATURE:
<221> NAME/KEY: misc_feature
<222> LOCATION: (1)..(1)
<223> OTHER INFORMATION: biotin at 5'

<400> SEQUENCE: 1
aaaaaaaaaa aaa                                                             13

<210> SEQ ID NO 2
<211> LENGTH: 13
<212> TYPE: DNA
<213> ORGANISM: Unknown
<220> FEATURE:
<223> OTHER INFORMATION: exemplary sequence used to illustrate
      invention
<220> FEATURE:
<221> NAME/KEY: misc_feature
<222> LOCATION: (1)..(1)
<223> OTHER INFORMATION: biotin at 5'

<400> SEQUENCE: 2
gggggggggg ggg                                                             13

<210> SEQ ID NO 3
<211> LENGTH: 25
<212> TYPE: DNA
<213> ORGANISM: Unknown
<220> FEATURE:
<223> OTHER INFORMATION: exemplary sequence used to illustrate
      invention
<220> FEATURE:
<221> NAME/KEY: misc_feature
<222> LOCATION: (1)..(1)
<223> OTHER INFORMATION: biotin at 5'

<400> SEQUENCE: 3
gcctccacgc acgttgtgat atgta                                                25

<210> SEQ ID NO 4
<211> LENGTH: 25
<212> TYPE: DNA
<213> ORGANISM: Unknown
<220> FEATURE:
<223> OTHER INFORMATION: exemplary sequence used to illustrate
      invention
<220> FEATURE:
<221> NAME/KEY: misc_feature
<222> LOCATION: (1)..(1)
<223> OTHER INFORMATION: biotin at 5'

<400> SEQUENCE: 4
ttcatatcac aacgtgcgtg gaggc                                                25

<210> SEQ ID NO 5
<211> LENGTH: 8
<212> TYPE: DNA
<213> ORGANISM: Unknown
<220> FEATURE:
<223> OTHER INFORMATION: exemplary sequence used to illustrate
      invention

<400> SEQUENCE: 5 gggggggg                                                                    8

<210> SEQ ID NO 6
<211> LENGTH: 8
<212> TYPE: DNA
<213> ORGANISM: Unknown
<220> FEATURE:
<223> OTHER INFORMATION: exemplary sequence used to illustrate
```

```
      invention

<400> SEQUENCE: 6 cccccccc                                                              8

<210> SEQ ID NO 7
<211> LENGTH: 10
<212> TYPE: DNA
<213> ORGANISM: Unknown
<220> FEATURE:
<223> OTHER INFORMATION: exemplary sequence used to illustrate
      invention

<400> SEQUENCE: 7
tttttttttt                                                           10

<210> SEQ ID NO 8
<211> LENGTH: 10
<212> TYPE: DNA
<213> ORGANISM: Unknown
<220> FEATURE:
<223> OTHER INFORMATION: exemplary sequence used to illustrate
      invention

<400> SEQUENCE: 8
aaaaaaaaaa                                                           10

<210> SEQ ID NO 9
<211> LENGTH: 10
<212> TYPE: DNA
<213> ORGANISM: Unknown
<220> FEATURE:
<223> OTHER INFORMATION: exemplary sequence used to illustrate
      invention

<400> SEQUENCE: 9
gggggggggg                                                           10

<210> SEQ ID NO 10
<211> LENGTH: 10
<212> TYPE: DNA
<213> ORGANISM: Unknown
<220> FEATURE:
<223> OTHER INFORMATION: exemplary sequence used to illustrate
      invention

<400> SEQUENCE: 10
cccccccccc                                                           10

<210> SEQ ID NO 11
<211> LENGTH: 24
<212> TYPE: DNA
<213> ORGANISM: Unknown
<220> FEATURE:
<223> OTHER INFORMATION: exemplary sequence used to illustrate
      invention

<400> SEQUENCE: 11
gcctccacga cgttgtgata tgta                                           24

<210> SEQ ID NO 12
<211> LENGTH: 24
```

-continued

```
<212> TYPE: DNA
<213> ORGANISM: Unknown
<220> FEATURE:
<223> OTHER INFORMATION: exemplary sequence used to illustrate
      invention

<400> SEQUENCE: 12
tacatatcac aacgtgcgtg gagg                                          24
```

METHOD FOR DETECTING TARGET BIOLOGICAL MATERIAL USING DNA BARCODES

CLAIM OF PRIORITY

This application claims the benefit of Korean Patent Application No. 2006-123353 filed on Dec. 6, 2006 in the Korean Intellectual Property Office, the disclosure of which is incorporated herein by reference.

BACKGROUND OF THE INVENTION

1. Field of the Invention

The present invention relates to a method for detecting a target biological material, and more specifically to a method for detecting a target biological material (e.g., DNA) using DNA barcodes by which a trace amount of the target biological material can be detected in a rapid and economical manner without performing polymerase chain reaction (PCR).

2. Description of the Related Art

A biochip or biosensor is designed so that various probes, such as DNA, antibodies, enzymes or cells, are immobilized on the surface of immobilization supports to allow an analyte of interest to specifically bind to the probes. Such a biochip or biosensor can be used to enable diagnosis of a disease using a small amount of a sample and to facilitate experiments, such as high throughput screening (HTS) and enzymatic activity measurement, on a large scale.

Many detection systems have been developed since the 1980's. Most of the early detection systems have a limitation in the amount of biological materials capable of being bound to immobilization supports and suffered from many difficulties in their commercialization because of expensive isotopes as main materials for analysis and problems in terms of safety. Since the early 1990's, many methods have been reported wherein fluorescent materials are used instead of isotopes and many kinds of biological materials can be immobilized in large amounts. Until now, remarkable progress has been made in the development of biochips and biosensors.

It is known that biochips and biosensors hitherto developed present the following drawbacks: 1) methods based on label-free analysis have the advantage of low cost but offer the problems of limited selectivity and low sensitivity; 2) labeling methods are disadvantageous because of increased cost; 3) there is the possibility of binding to materials other than analytes of interest in samples; and 4) when general analytical methods are employed for the analysis of DNA as an analyte of interest, a costly amplification technique (e.g., PCR amplification) is needed to increase the sensitivity of the analysis.

Numerous attempts to solve these problems have been made. For example, a new concept of amplification of signals using DNA barcodes was introduced by Mirkin, a professor at Northwestern University, USA. Based on this concept, trace amounts of samples at attomolar levels can currently be analyzed without performing PCR. However, Mirkin's technique requires the use of expensive materials (e.g., gold) and involves a complicated procedure associated with the formation of platforms. Several modifications to Mirkin's technique are being introduced.

According to several methods that have recently been introduced, gold nanoparticles (NRs) binding to two types of short DNA and magnetic particles (MMPs) binding to one type of DNA are mainly used and amplified DNA signals are analyzed by a chip-based-detection method. Analytical results of the methods obtained prostate specific antigen (PSA) demonstrate that the antigen can be analyzed at attomolar levels ($10^{18}$ M). However, currently used methods also necessitate the use of nanoparticles and gold particles. Under these circumstances, continuous efforts are being made towards cost reduction and simplification of the analytical procedure.

SUMMARY OF THE INVENTION

The present invention has been made to solve the foregoing problems of the prior art and therefore an aspect of the present invention is to provide a method for detecting a target biological material using DNA barcodes by which the target biological material can be detected in a more rapid and economical manner.

According to an aspect of the present invention, the present invention provides a method for detecting a target biological material using DNA barcodes, the method comprising:

attaching a first type of probes to the surface of magnetic particles to prepare magnetic particles for isolation wherein the first type of probes are at least partially complementary to a target biological material of interest;

attaching a second type of probes to the surface of polymer particles to prepare polymer particles for analysis wherein the second type of probes are at least partially complementary to the target material but are different from the first type of probes, and attaching DNA barcodes as identification codes to the surface of the polymer particles wherein the DNA barcodes are present in an amount at least three times the amount of the second type of probes, have a predetermined sequence and are labeled with a label material;

reacting the magnetic particles for isolation, the polymer particles for analysis and the target material in a hybridization reaction buffer to prepare composites, each of which consists of one magnetic particle for isolation, the target material and one polymer particle for analysis;

separating the composites from unreacted reactants using a magnetic separator;

heating the separated composites to denature the DNA barcodes present in the polymer particles for analysis and removing the magnetic particles for isolation and the polymer particles for analysis from the composites by centrifugation to isolate the DNA barcodes; and detecting a signal generated from the label material bound to the isolated DNA barcodes.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Exemplary embodiments of the present invention will now be described in detail.

The present invention provides a method for detecting a target biological material (e.g., DNA) using magnetic particles for isolation whose surface is coated with probes complementary to the target material and polymer particles for analysis whose surface is coated with DNA (barcode DNA or biobarcode DNA) having a predetermined sequence as an identification code.

The method of the present invention is characterized by the use of magnetic particles and polymer particles coated with DNA barcodes to sensitize a trace amount of a biological material (e.g., DNA). The magnetic particles used in the method of the present invention are coated with a first type of probes partially complementary to a target material (e.g., a DNA target) of interest. The polymer particles used in the method of the present invention are coated with a second type of probes having a sequence different from that of the first type of probes but capable of complementary binding to the target material of interest and are coated with DNA barcodes. Accordingly, when the target material is added to a solution containing a mixture of the two kinds of the particles, it serves to link the two kinds of the particles. The linked particles are separated using a magnet to obtain composites consisting of the magnetic/polymer particles. When DNA capable of complementary binding to the DNA barcodes is added to the isolated composites, the amount of the DNA bound to the composites is proportional to both the number of the magnetic/polymer particles and the amount of the target material bound to the composites. The bound DNA barcodes are isolated from the composites consisting of the magnetic/polymer particles and analyzed. The analytical results indicate that a much stronger signal is obtained than when the target material is directly analyzed. As a result, the method of the present invention enables the analysis of a trace amount of DNA, and allows simultaneous isolation and analysis, which contributes to a considerable reduction in the time and cost required to analyze the DNA.

The target biological material of interest is preferably an oligonucleotide or a protein. Specific examples of suitable target biological materials include DNA, RNA, antigens, antibodies and haptens.

The magnetic particles for isolation act to isolate the target material of interest from a sample, the polymer particles for analysis are designed such that a signal generated from the target material can be amplified. Explanations of the particles for isolation and the particles for analysis used in the method of the present invention will be provided below with reference to the accompanying drawings.

Magnetic Particles for Isolation

Figure 1:
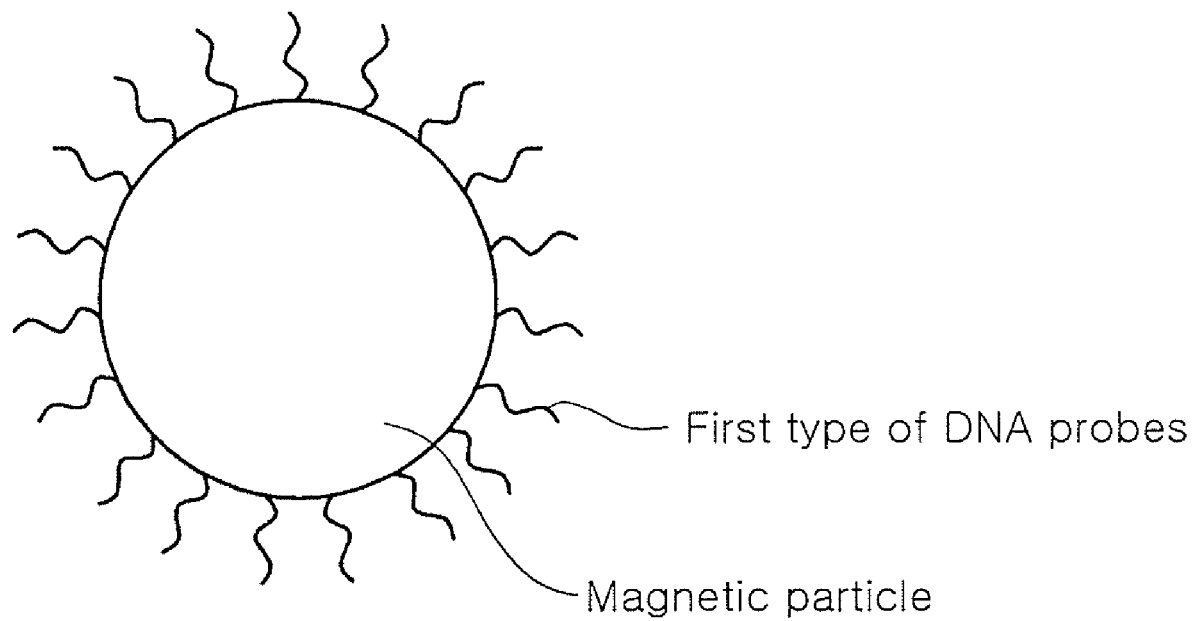
FIG. 1 shows a magnetic particle for isolation used in a method of the present invention.

The magnetic particles for isolation are prepared by attaching a first type of probes to the surface of magnetic particles wherein the first type of probes are at least partially complementary to a target biological material of interest. One of the magnetic particles for isolation is shown in FIG. 1.

Each of the particles for isolation is composed of a magnetic particle and a first type of probes capable of partially complementary binding to a target material. The first type of probes are attached to the surface of the magnetic particles. The first type of probes may be bound to the magnetic particles through covalent or non-covalent interactions.

The first type of probes attached to the surface of the magnetic particles are preferably oligonucleotides or proteins. Specific examples of such probes include DNA, RNA, PNA, aptamers, antigens, antibodies and haptens. The first type of probes may be directly attached to the surface of the magnetic particles. Alternatively, the surface of the magnetic particles may be modified using a surface-treating material, which acts as a linker for the subsequent attachment of the first type of probes to the magnetic particles. The use of the surface-treating material is preferred in terms of attachment efficiency. As the surface-treating material, a silane, epoxy, carboxyl, amine or aldehyde material may be used. Specific examples of suitable surface-treating materials include aminopropyltriethoxysilane (APTES), glycidoxypropyltrimethoxysilane (GPTS), triethoxysilane undecanoic acid (TETU), poly(lysine), and 4-trimethoxysilylbenzaldehyde. Avidin or streptavidin may also be used to coat the magnetic particles.

Then, the coated magnetic particles are bound by the first type of probes partially complementary to a target material. It is preferred that the reaction precursors remaining after the binding undergo recycling before being discharged to ensure no influence on the analysis of the target material. The binding of the first type of probes to the magnetic particles may be achieved through various methods. In an embodiment where the first type of probes are DNAs, one end of each DNA is coated with biotin and the particles are coated with streptavidin. The binding is achieved by reacting the magnetic particles with the probes. Further, the binding between the magnetic particles and the first type of probes may be achieved by various binding methods, such as amine-succinyl anhydride binding and PNA-DNA binding. The reaction precursors remaining after the binding may be separated using magnetic particles as magnets and a filtrate may be discharged. Alternatively, the residual reaction precursor particles may be collected by centrifugation and a filtrate may be discharged.

The first type of probes are partially complementary to a target biological material of interest. The first type of probes preferably have a homology of at least 30%, more preferably a homology of at least 40% and most preferably a homology of 40% to 60% with the target material.

The number of the first type of probes attached to each of the magnetic particles may vary from several tens to several hundreds, but is not limited to thereto. The first type of probes may have different lengths. The length of the first type of probes may vary depending on the types of the target material and the probes, and those skilled in the art will readily determine the optimal length of the first types of probes under given conditions. For example, if the first type of probes are DNAs, they have a maximum length corresponding to 25% of the length of the nucleotide sequence of the target material or 10 mer or more base pairs. On the other hand, any magnetic material that allows easy attachment of the first type of probes can be used to prepare the magnetic particles. It is preferred to coat a material for the magnetic particles with a polymer having a moiety, such as streptavidin, COOH, OH, $SiO_x$ or $NH_2$, so that the moiety can be exposed to the surface of the magnetic particles. The magnetic particles are preferably those having superparamagnetic properties. Examples of such superparamagnetic particles include, but are not limited to, particles of iron-oxide, iron-cobalt, iron-nickel and transition metals.

The shape of the magnetic particles is preferably spherical. Since the size of the magnetic particles must vary depending on the concentration and kind of the analyte of interest, there is no need to limit the size of the magnetic particles. For better separation of the magnetic particles by using a typical magnet, the magnetic particles preferably have a diameter of 0.1 to 100 μm, more preferably 1.0 to 2.8 μm, and most preferably 1.0 μm.

Polymer Particles for Analysis

Figure 2:
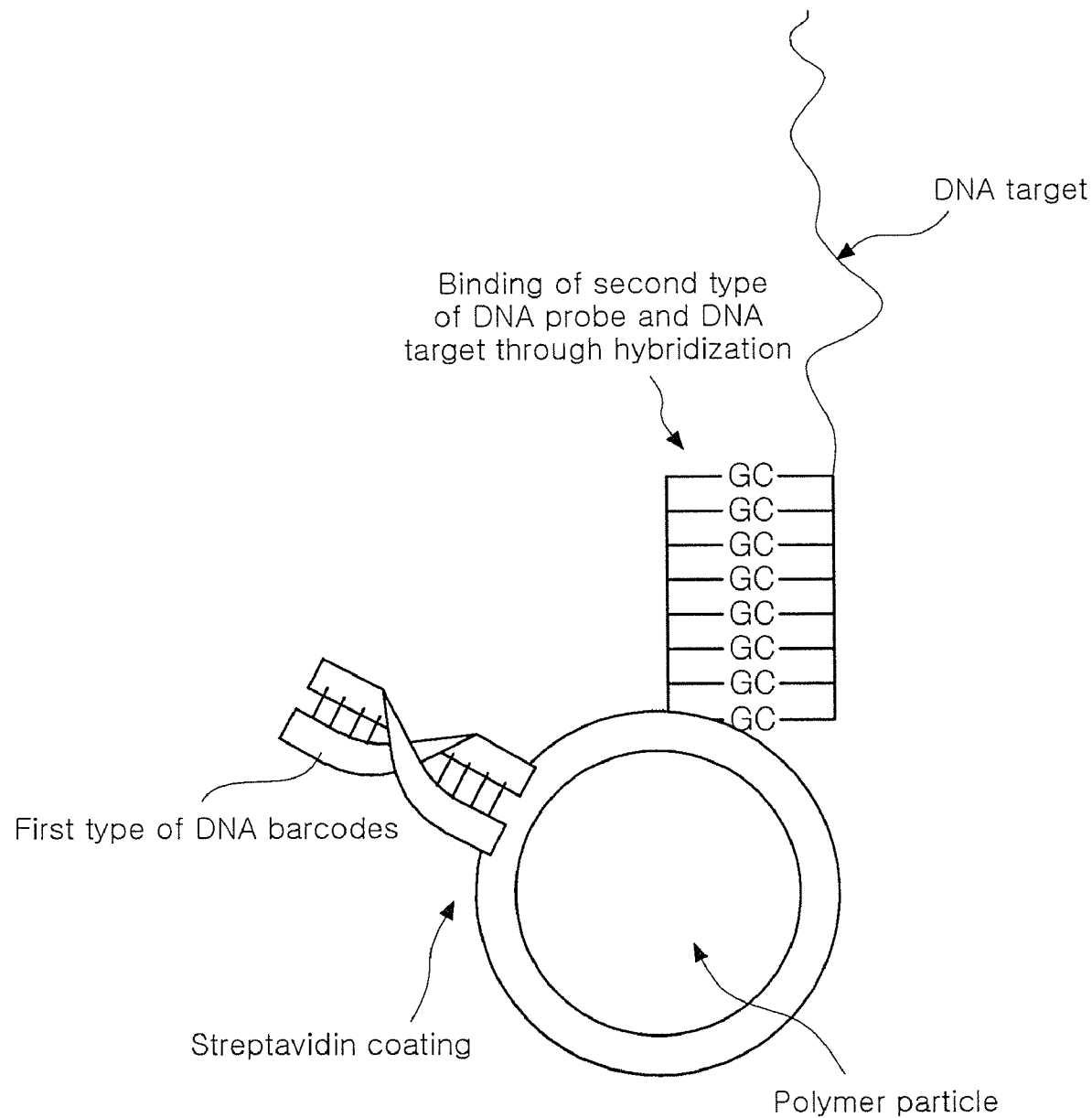
FIG. 2 shows a polymer particle for analysis used in a method of the present invention wherein the sequences are shown for illustrative purposes and relate to SEQ ID NO:5 (GGGGGGGG) and to SEQ ID NO:6 (CCCCCCCC) of the Sequence Listing.

The polymer particles for analysis are prepared by attaching a second type of probes to the surface of polymer particles wherein the second type of probes are at least partially complementary to the target material but are different from the first type of probes, and attaching DNA barcodes as identification codes to the surface of the polymer particles wherein the DNA barcodes are present in an amount at least three times the amount of the second type of probes, have a predetermined sequence and are labeled with a label material. One of the polymer particles for analysis is shown in FIG. 2.

The particles for analysis can be partially bound to the target material. Each of the particles is composed of i) a second type of probes binding to the target material at sites different from binding sites of the target material binding and the first type of probes, and ii) DNA barcodes for signal amplification. The second type of probes and the DNA barcodes are attached to the surface of the polymer particles. The second type of probes and the DNA barcodes may be bound to the polymer particles through covalent or non-covalent interactions.

The second type of probes attached to the surface of the polymer particles are preferably oligonucleotides or proteins. Specific examples of such probes include DNA, RNA, PNA, aptamers, antigens, antibodies and haptens. The second of probes may be directly attached to the surface of the particles. Alternatively, the surface of the polymer particles may be modified using a surface-treating material, which acts as a linker for the subsequent attachment of the second type of probes to the polymer particles. The use of the surface-treating material is preferred in terms of attachment efficiency. As the surface-treating material, a silane, epoxy, carboxyl, amine or aldehyde material may be used. Specific examples of suitable surface-treating materials include aminopropyltriethoxysilane (APTES), glycidoxypropyltrimethoxysilane (GPTS), triethoxysilane undecanoic acid (TETU), poly(lysine), and 4-trimethoxysilylbenzaldehyde. Avidin or streptavidin may also be used to coat the polymer particles.

The second type of probes are partially complementary to the target biological material of interest. The second type of probes preferably have a homology of at least 25% and more preferably a homology of 40% to 50% with the target material.

The number of the second type of probes attached to each of the polymer particles may vary from several tens to several hundreds, but is not limited to thereto. The second type of probes may have different lengths. The length of the second type of probes may vary depending on the types of the target material and the probes, and those skilled in the art will readily determine the optimal length of the second types of probes under given conditions. For example, if the second type of probes are DNAs and the target material is a DNA, they have a length corresponding to about 25% of the length of the DNA target.

On the other hand, any polymeric material that allows easy attachment of the second type of probes can be used to prepare the polymer particles. Examples of preferred materials for the polymer particles include silica, latex, polystyrene (PS), polyethyleneimine (PEI), and dextran. The molecular weight and size of the polymer particles must be varied depending on the concentration and kind of the analyte of interest, there is no need to limit the molecular weight and size of the polymer particles. For example, the polymeric material may be polyethyleneimine having a molecular weight of about 60,000 and preferably about 1,000,000, but is not limited thereto. The shape of the polymer particles is preferably spherical. The average diameter of the polymer particles is preferably in the range of 0.1 to 1.0 μm, but is not limited to this range.

The DNA barcodes attached to the surface of the polymer particles are present in an amount much larger than that of the second type of probes. For example, the DNA barcodes are present in an amount at least three times the amount of the second type of probes. The ratio of the number of the DNA barcodes to the number of the second type of probes is preferably between 3:1 and 1,000:1, but is not limited to this range.

The DNA barcodes may be double stranded DNAs, each of which consists of a first type of barcode DNA and a second type of barcode DNA complimentary to the first type of barcode DNA. One end of the first type of barcode DNA is labeled with a label material and the other end of the first type of barcode DNA is attached to the surface of the polymer particles. One end of the second type of barcode DNA is attached to the surface of the polymer particles. The label material may be any material that can be detected using commercially available systems. The label material may be a nanosized magnetic particulate material, a material that can be analyzed based on fluorescence, or a material whose surface is negatively charged. Examples of such label materials include magnetic nanoparticles, fluorescent materials, and quantum dots.

If the number of the first type of probes binding to the magnetic particles is greater than that of the magnetic particles, there is no influence on the analysis. Taking into consideration the purpose of the analysis, the ratio of the number of the second type of probes to the number of the DNA barcodes attached to the surface of the polymer particles is preferably adjusted to 1:1,000 or more. The reason why the ratio must be accurately adjusted is because the ratio between the second type of probes and the DNA barcodes will be an amplification ratio of a signal generated from the final platforms.

Thereafter, the magnetic particles for isolation, the polymer particles for analysis and the target material are allowed react in a hybridization reaction buffer. The target material may be separately added to a solution of the particles for isolation and a solution of the particles for analysis. Alternatively, a solution of the particles for isolation is mixed with a solution of the particles for analysis, and then the target material is added to the mixture. The resulting mixture is subjected to a hybridization reaction for a time sufficient to allow the target material to react with both the particles for isolation and the particles for analysis.

Figure 3:
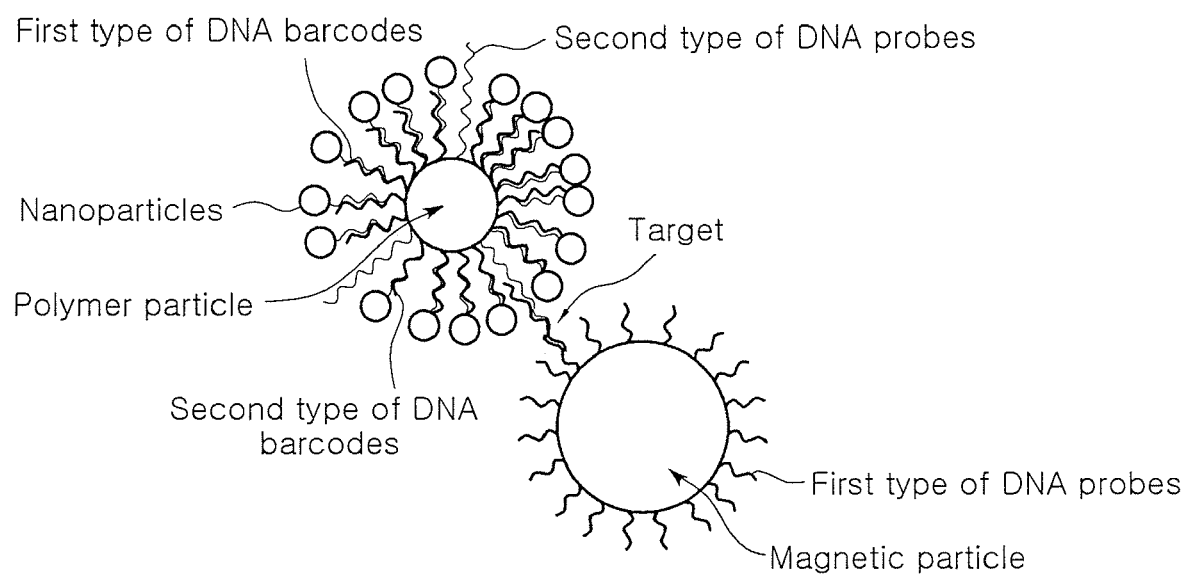
FIG. 3 shows a composite consisting of a magnetic particle for isolation, a target material and a polymer particle for analysis.
Figure 4:
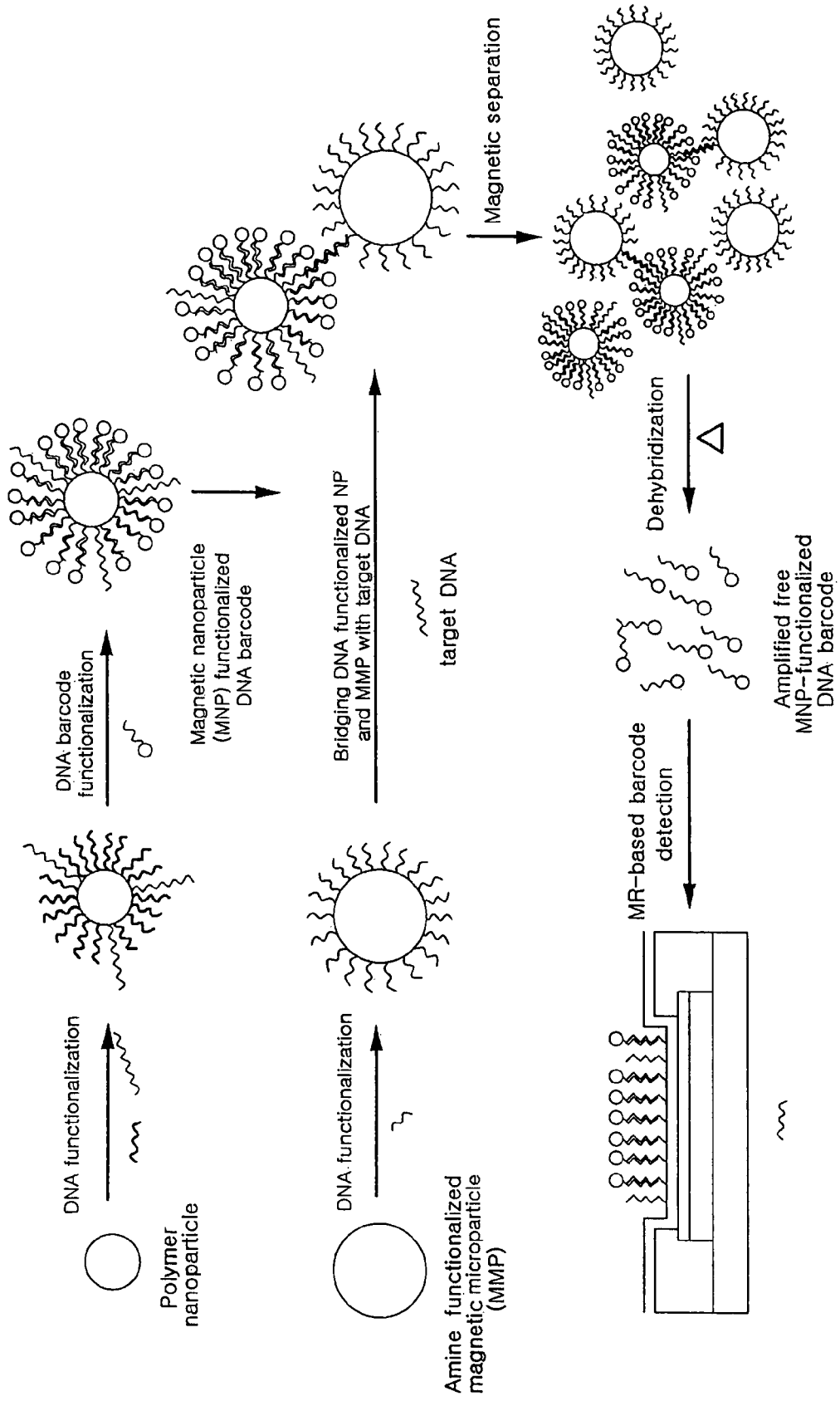
FIG. 4 schematically illustrates a method for detecting a target biological material using DNA barcodes according to the present invention.

The hybridization reaction may be conducted in a TE solution or any solution that can cause the hybridization reaction at room temperature for 1.5 to 2 hours. The hybridization reaction is completed to form composites, each of which consists of one magnetic particle for isolation, the target material and one polymer particle for analysis. One of the composites is shown in FIG. 3.

Then, the composites are separated from the unreacted reactants by magnetic separation. The magnetic separation may be performed using a general separation separator.

Thereafter, the composites thus separated are heated to denature the DNA barcodes present in the polymer particles for analysis. The denatured DNA barcodes are precipitated. The magnetic particles for isolation and the polymer particles for analysis are removed from the composites by centrifugation to isolate the DNA barcodes.

The heating may be conducted at a temperature higher than the melting temperature ($T_m$) of the DNA barcodes to denature the DNA barcodes. Those skilled in the art can readily recognize and simply calculate the $T_m$ of the DNA barcodes.

Subsequently, a signal generated from the label material bound to the isolated DNA barcodes is detected. As is known in the art, methods for detecting the signal generated from the label material may vary depending on the characteristics of the label material. That is, the isolated DNA barcodes may be analyzed by various methods. If the DNA barcodes are labeled with magnetic nanoparticles, analysis is done using a giant magneto resistive (GMR) sensor. The amount of the DNA barcodes may be measured by fluorescence or general chemical analysis.

In an embodiment of the present invention, the DNA probes are designed such that they are complementarily bound to only a portion of the DNA target. The DNA target is an analyte of interest and acts as a linker capable of binding the two kinds of the particles. The linked particles are separated using a magnet to obtain composites consisting of the magnetic/polymer particles. When DNA capable of complementary binding to the DNA barcodes is added to the isolated composites, the amount of the DNA bound to the composites is proportional to both the number of the magnetic/polymer particles and the amount of the DNA target bound to the composites. Accordingly, the DNA barcodes are present in an amount much larger than that of the DNA target in the isolated composites consisting of the magnetic/polymer particles. When unbound free particles are removed using a magnetic force, the amount of the DNA barcodes bound to the polymer particles is from several tens of times to several thousands of times larger than that of the DNA target. The DNA barcodes bound to the polymer particles in proportion to the amount of the DNA target are isolated and analyzed. As a result, an amplified signal is obtained on the amount of the DNA barcodes larger than that of the DNA target. The amount of the DNA target can be indirectly identified by calculating back from the signal. This analysis may be achieved using the label material (e.g., magnetic nanoparticles, a fluorescent material and quantum dots) bound to the DNA barcodes or by label-free methods. In this manner, a trace amount of DNA at sub-femtomolar or sub-attomolar level can be analyzed without performing costly amplification techniques, such as PCR amplification.

Conventional methods for detecting target biological materials using particles simply emphasize the separation of the target materials from samples. In contrast, the detection method of the present invention allows a target material to be simultaneously isolated and analyzed by effectively using two kinds of particles, thus achieving a reduction in the time and cost required to analyze the target material as well as enabling a marked increase in sensitivity by the use of a barcode material. The platforms proposed in the method of the present invention can be used for general purposes, irrespective of the kind of detectors. In addition, the method of the present invention can be advantageously used to detect a trace amount of a biological material (e.g., DNA) in a rapid and economical manner without using any expensive material, such as gold.

Hereinafter, the present invention will be explained in more detail with reference to the following examples.

EXAMPLES

Example 1

First, oligonucleotides having the base sequences set forth in Table 1, magnetic particles (for isolation) having a diameter of 2.8 µm, and polymer particles (for analysis) having a diameter of 0.5 µm were prepared. The magnetic particles had a core composed essentially of iron oxide and a surface coated with streptavidin (Dyna-280, Invitrogen). As the polymer particles, silica particles (CS01N/7659, Bang's lab) were used. Both the magnetic particles and the polymer particles were coated with streptavidin to allow the oligonucleotides, each of which had a biotin end, to be bound to the two kinds of the particles.

TABLE 1

| Type of DNA | sequence |
| --- | --- |
| First type of probes | 5'-biotin AAA AAA AAA AAAA-3' |
| Second type of probes | 5'-biotin GGG GGG GGG GGGG-3' |
| First type of DNA barcodes (c-Barcodes) | 5'-biotin GCC TCC ACG CAC GTT GTG ATA TGT A-3' |
| Second type of DNA barcodes (Barcodes) | 3'-CGG AGG TGC GTG CAA CAC TAT ACT T biotin-5' |

The sequences in TABLE 1 relate to the following sequence identification numbers in the Sequence Listing: 1. SEQ ID NO:1; 2. SEQ ID NO:2; 3. SEQ ID NO:3; and 4. SEQ ID NO:4.

DNA whose both ends were replaced with thymine (T) and cytidine (c) was used as a target so that it could be partially complementarily bound to one end of the first type of probes and one end of the second type of probes.

Taking into consideration the amount of the streptavidin bound to the magnetic particles, the first type of probes were diluted and mixed with the magnetic particles (200 pmole per $6.05 \times 10^7$ counts of the magnetic particles). Thereafter, unreacted first type of DNA probes and the remaining magnetic particles were separated using a magnetic separator (Invitrogen, Dynal MPC) in accordance with the manufacturer's manual, and removed.

The second type of DNA probes, the first type of DNA barcodes (c-barcodes) and the second type of DNA barcodes (barcodes) were allowed to bind to the silica particles. To avoid occurrence of unnecessary competitive reactions, the second type of DNA probes, the first type of DNA barcodes (c-barcodes) and the second type of DNA barcodes (barcodes) were applied in this order. First, the second type of DNA probes were applied at the same concentration as the silica beads applied (in a ratio of about 3.7 femtomoles to 3.7 attomoles). After completion of the streptavidin-biotin reaction, the first type of DNA barcodes were applied. The streptavidin-biotin reaction was allowed to proceed in solutions of 10 mM Tris-HCL, 1.0 mM EDTA and 1 M NaCl for 15 minutes or more.

The second type of DNA barcodes were applied after the binding of the first type of DNA barcodes to the silica beads. The amount of the second type of DNA barcodes was preferably larger than the first type of DNA barcodes. The use of an excess of the second type of DNA barcodes caused no special problem because the second type of DNA barcodes would be removed in the subsequent isolation step.

Figure 10:
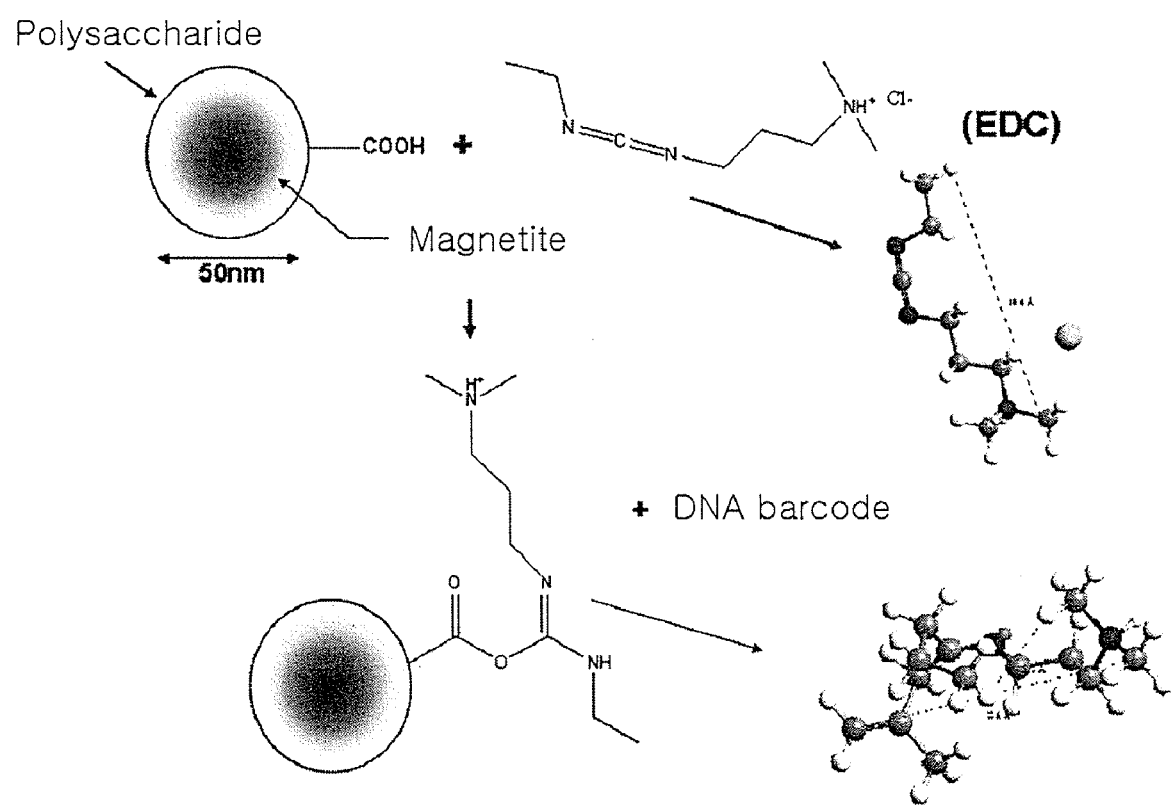
FIG. 10 is an exemplary diagram illustrating a method for labeling a DNA barcode with a magnetic nanoparticle.

The second type of DNA barcodes were labeled with nanosized magnetic particles. This labeling is shown in FIG. 10. For example, the attachment of the DNA barcodes to the nanosized magnetic particles was performed using 1-ethyl-3-[3-dimethylaminopropyl]carbodimide hydrochloride (EDC). The surface of the nanosized magnetic particles was covered with a carboxyl group. One side of the EDC was bound to the nanosized beads, and the other side of the EDC was bound to an amine group. One end of the DNA was replaced with an amine group to allow the DNA to be bound to the nanosized beads.

The second type of DNA barcodes labeled with the nanosized beads were bound to the silica particles. The ratio of the number of the silica particles to the number of the second type of DNA barcodes labeled with the nanosized beads was adjusted to 1:1,000. The reaction was conducted using a TE buffer for 2 hours.

Immediately after the particles for isolation and the particles for analysis were mixed together in a ratio of 1:1, the DNA target was added thereto. The mixture was allowed to react. The reaction was conducted in a TE or B/W buffer for 2 hours. During the reaction, the formation of a precipitate was prevented by patting the reactor with a hand once every 10 minutes.

Figure 6:
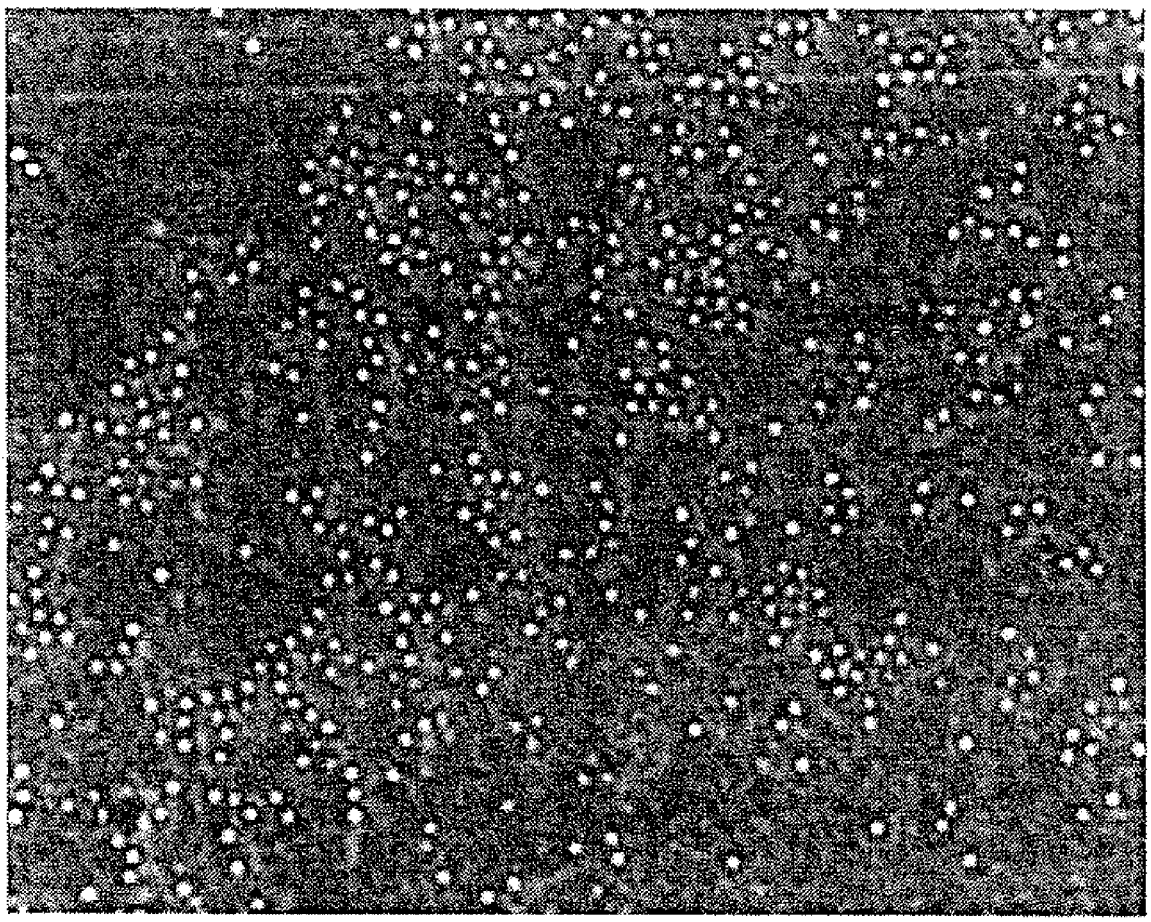
FIG. 6 is a fluorescence micrograph (magnification 200×) of magnetic particles for isolation used in Example 1 of the present invention.
Figure 7:
FIG. 7 is a fluorescence micrograph (magnification 1,000×) of composites, each of which consists of a magnetic particle for isolation, a target material and a polymer particle for analysis.

After completion of the reaction, the DNA target was bound to the two kinds of the particles to form platforms. One of the platforms is shown in FIG. 3. A fluorescence micrograph (magnification 200×) of unreacted particles for isolation is shown in FIG. 6. The platforms were stained, and a fluorescence micrograph of the stained platform was taken at a magnification of 1,000× (FIG. 7).

Figure 5:
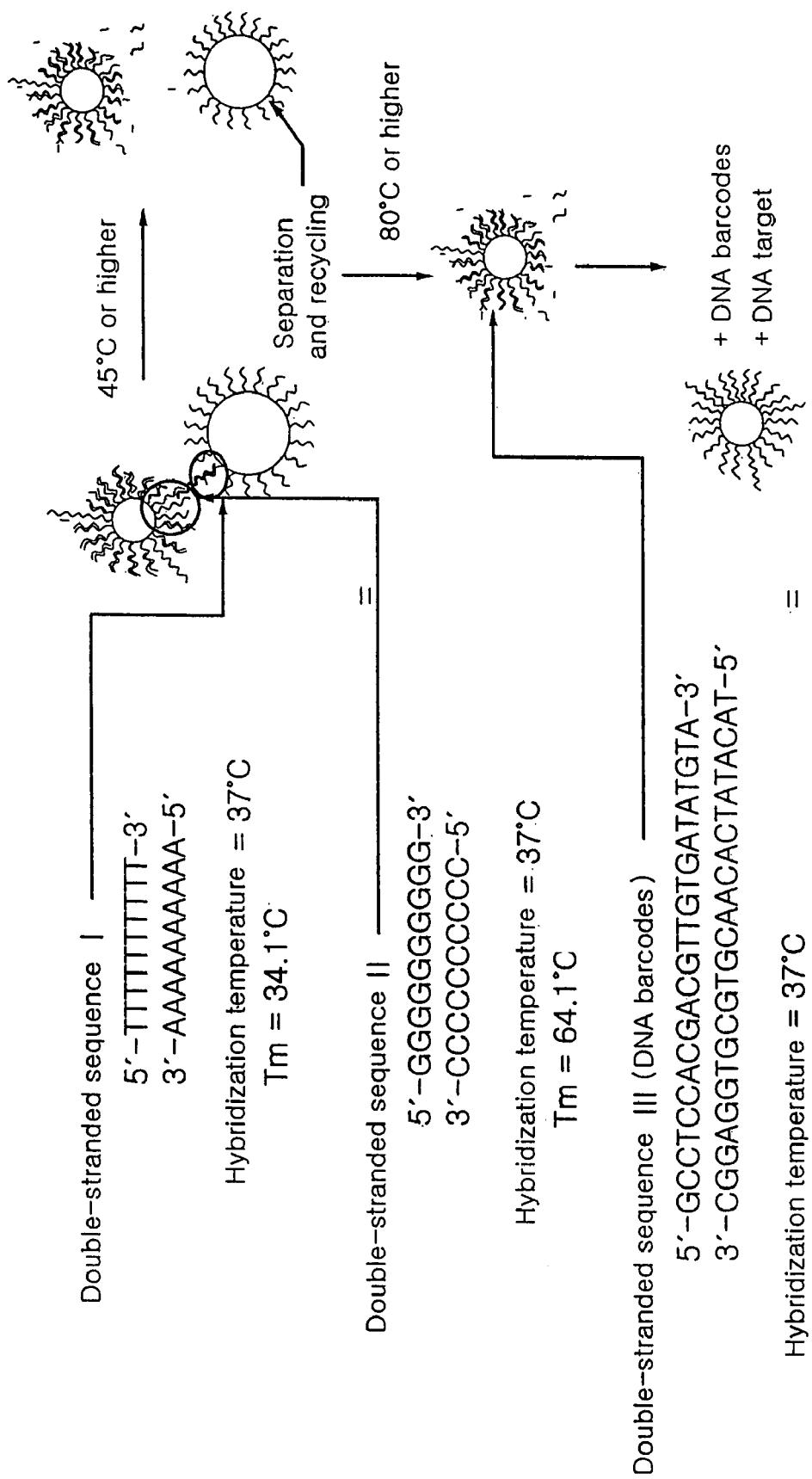
FIG. 5 schematically illustrates a procedure for isolating DNA barcodes from a composite consisting of a magnetic particle for isolation, a target material and a polymer particle for analysis in which the DNA barcodes are present in the polymer particle for analysis, and wherein the sequences are shown for illustrative purposes and are identified in the Sequence Listing as follows: SEQ ID NO:7 (TTTTTTTTTT); SEQ ID NO:8 (AAAAAAAAAA); SEQ ID NO:9 (GGGGGGGGGG); SEQ ID NO:10 (CCCCCCCCCC); SEQ ID NO:11 (GCCTCCACGACGT-TGTGATATGTA); and SEQ ID NO: 12 (TACATATCA-CAACGTGCGTGGAGG)

After formation of the platforms, the second type of DNA barcodes bound to the polymer particles were isolated and analyzed (see, FIG. 5). In this example, the isolation was conducted at a temperature higher than the melting temperatures ($T_m$) of the first type of DNA barcodes and the second type of DNA barcodes. First, the particles for isolation were separated from the particles for analysis by heating to 45° C. or higher for 30 minutes. In accordance with the above method, a magnetic separator (Invitrogen, Dynal MPC) was used to separate the particles for isolation and collect the particles for analysis only. Then, the second type of DNA barcodes were isolated from the particles for analysis by heating to a temperature (80° C. or above) higher than $T_m$ of the particles for analysis for 30 minutes. The particles for analysis were removed from the sample by centrifugation at 12,000 rpm for 30 seconds.

Figure 8:
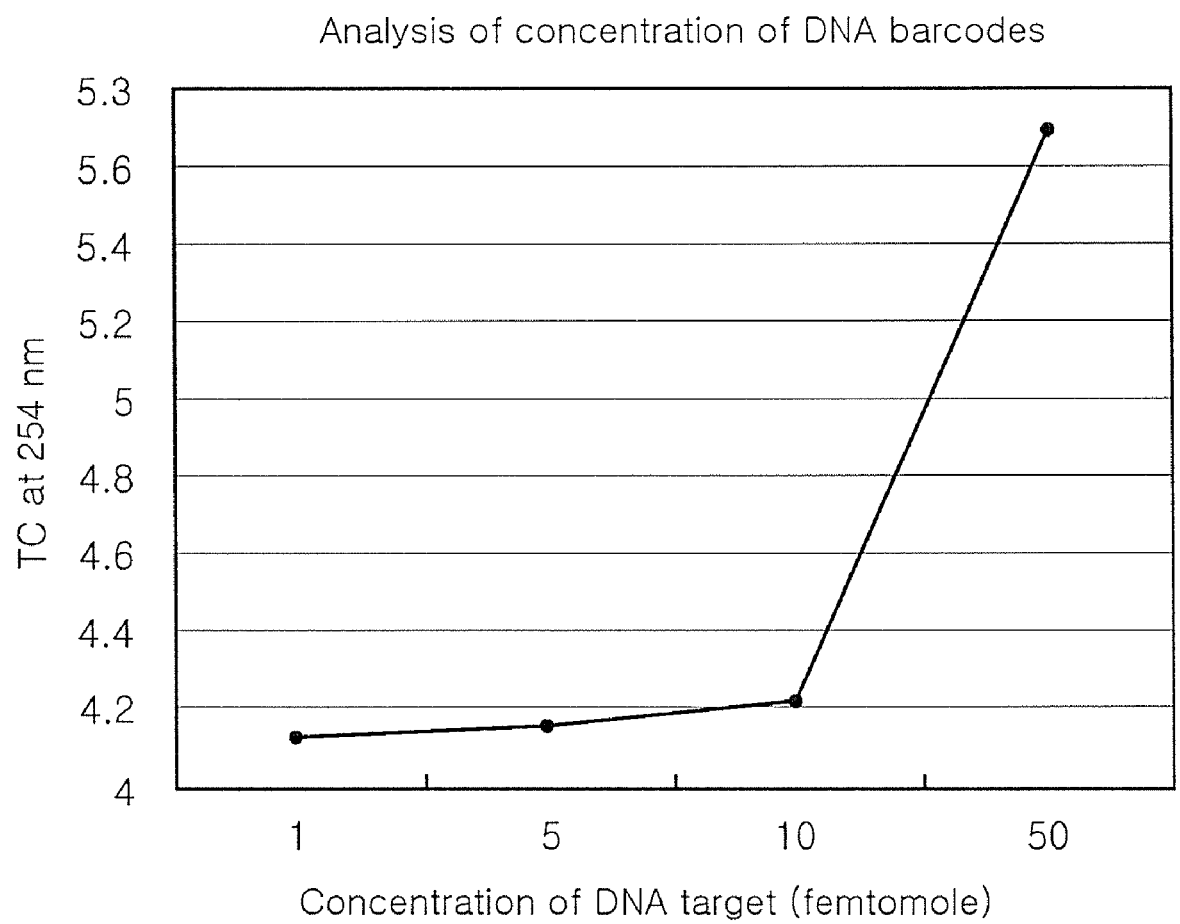
FIG. 8 is a graph showing variations in the amount of DNA barcodes detected with varying amounts of a DNA target at femtomolar levels.
Figure 9:
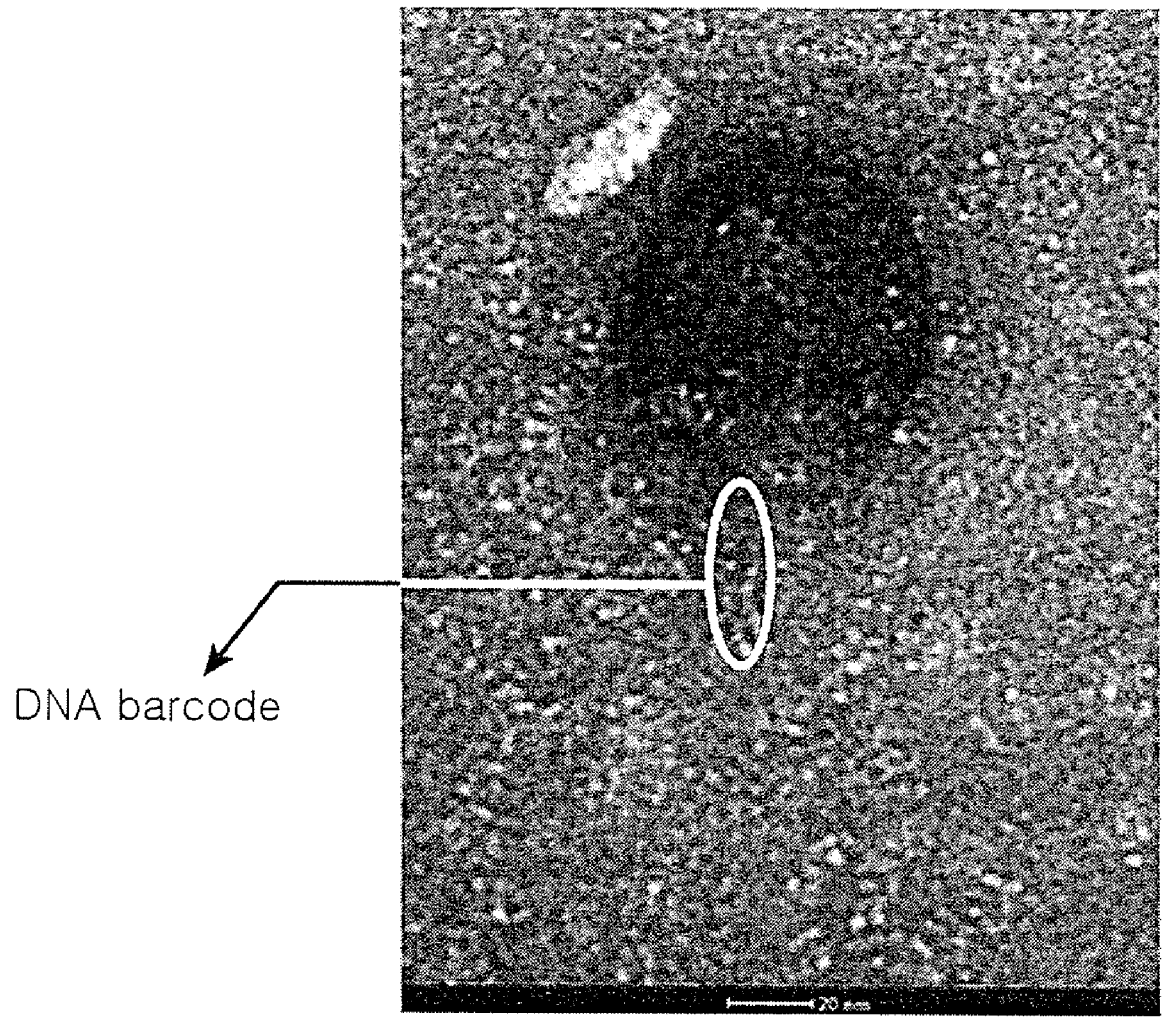
FIG. 9 is a transmission electron micrograph (TEM) of a conjugate consisting of a magnetic particle for isolation and DNA barcodes bound to the magnetic particle.
Figure 11:
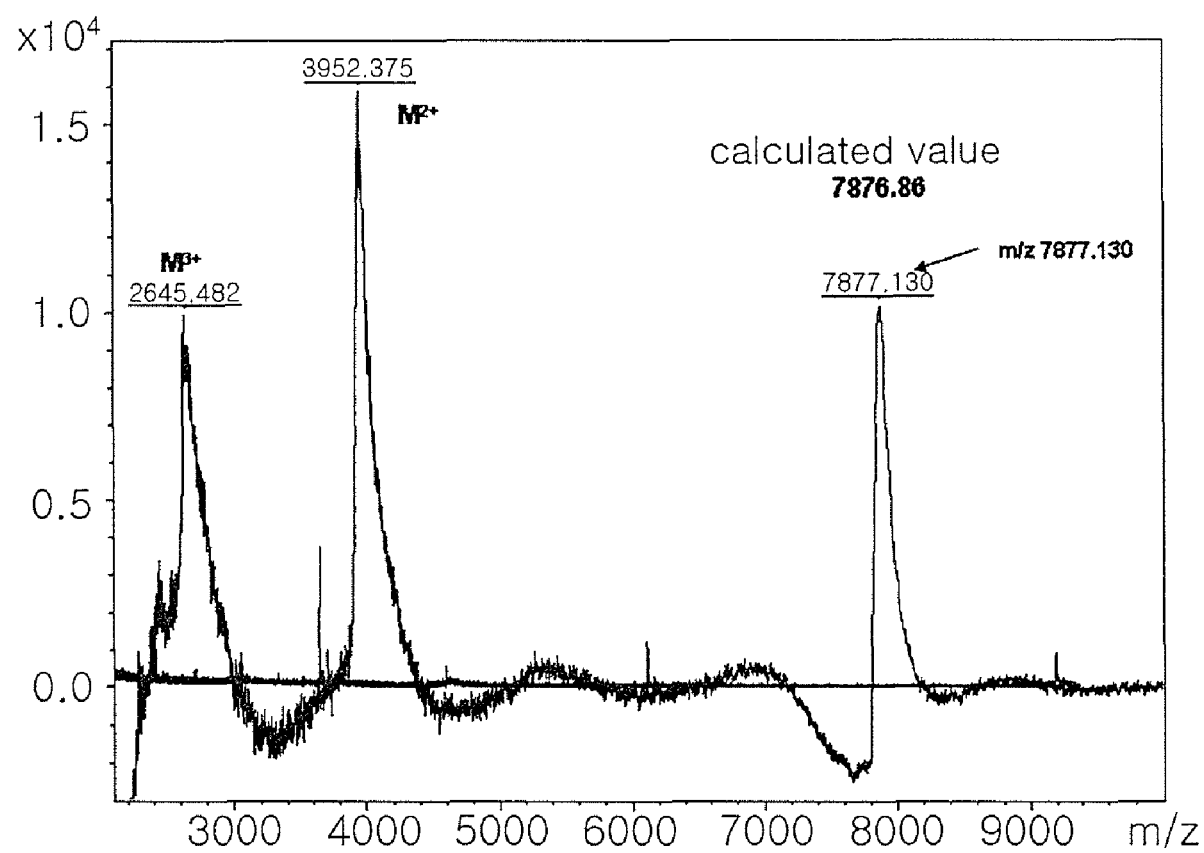
FIG. 11 is a graph showing analytical results of a second type of DNA barcodes isolated by matrix-assisted laser desorption ionization-time of flight (MALDI-TOF) mass spectrometry.
Figure 12:
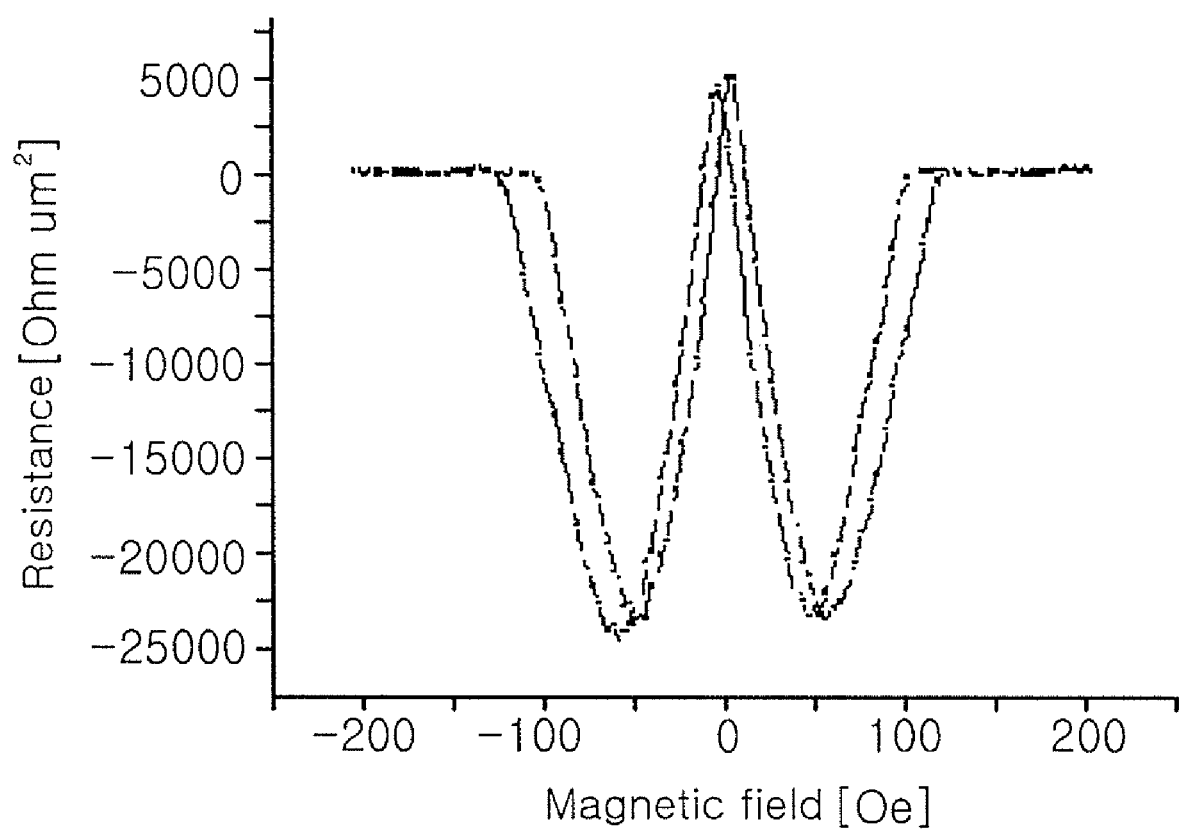
FIG. 12 is a graph showing analytical results of a second type of DNA barcodes isolated using a giant magneto resistive (GMR) sensor.
Figure 13:
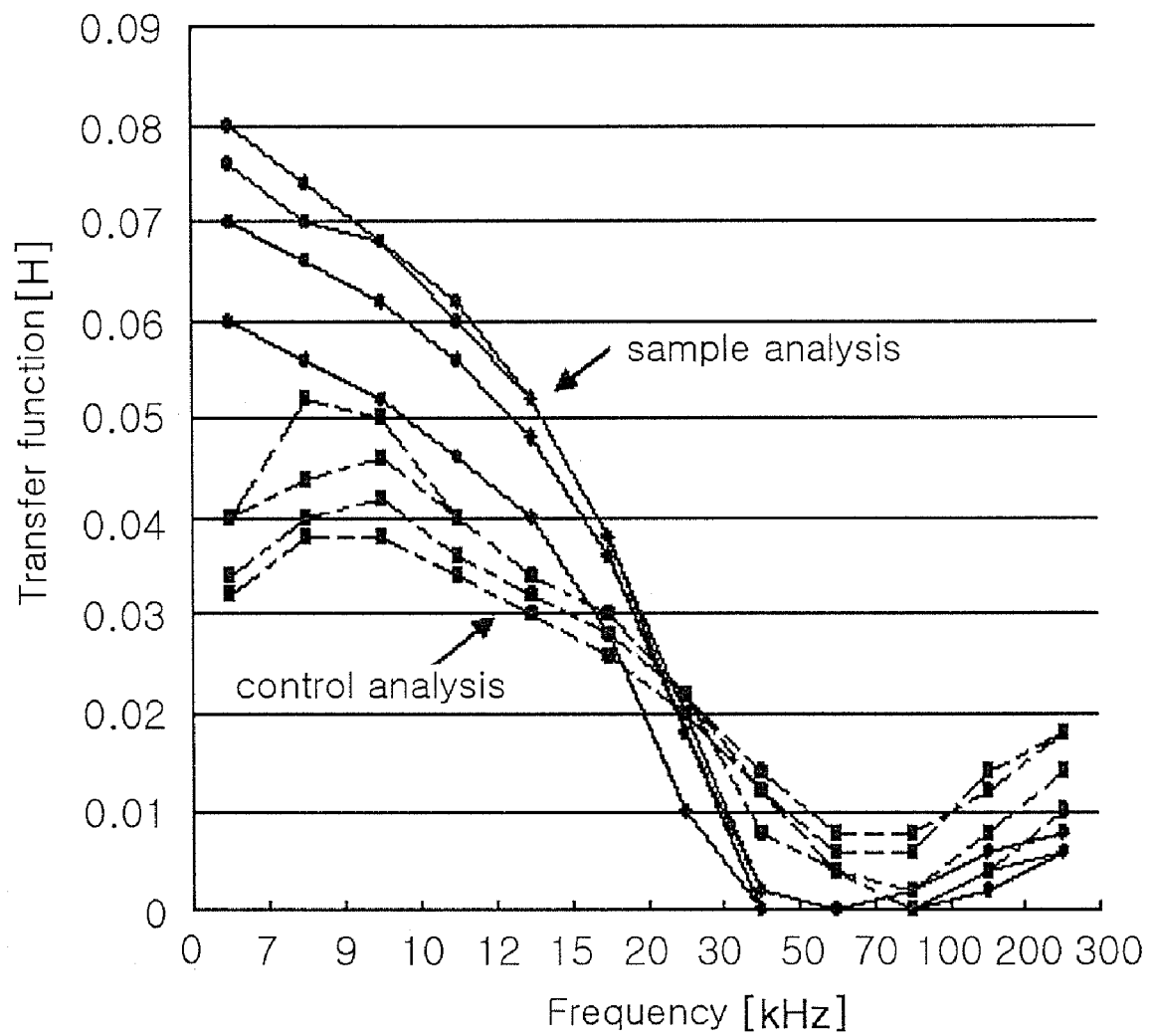
FIG. 13 is a graph showing analytical results of a second type of DNA barcodes isolated using a field effect transistor (FET).

The second type of DNA barcodes isolated and amplified from the platforms were analyzed by various methods, such as spectroscopy, magnetic analysis, mass analysis and chromatography. These experiments were conducted with varying amounts of the DNA target at femtomolar levels to analyze the amount of the DNA barcodes detected at the different amounts of the DNA target. The results are shown in FIG. 8. The mass analysis was performed by MALDI-TOF (FIG. 11). The magnetic analysis was performed by measuring resistance values using a GMR sensor (FIG. 12). The FET was used to measure voltage values, which were obtained from current values flowing from a source to a drain (FIG. 13). The control values shown in FIG. 13 imply values measured before the DNA was immobilized on the sensor.

As is evident from the graph of FIG. 8, the amount of the DNA barcodes detected was increased in proportion to the increase in the amount of the DNA target to femtomolar levels. This result indicates that the method of the present invention showed high detection sensitivity.

As apparent from the above description, according to the method of the present invention, a trace amount of DNA at femtomolar or attomolar level can be analyzed without performing costly amplification techniques, such as PCR amplification.

While the present invention has been shown and described in connection with the exemplary embodiments, it will be apparent to those skilled in the art that modifications and variations can be made without departing from the spirit and scope of the invention as defined by the appended claims.

What is claimed is:

1. A method for detecting a target biological material using DNA barcodes, the method comprising:
   attaching a first type of DNA probes to the surface of magnetic particles to prepare magnetic particles for isolation wherein the first type of DNA probes are at least partially complementary to a DNA target biological material of interest;
   attaching a second type of DNA probes to the surface of polymer particles to prepare polymer particles for analysis wherein the second type of DNA probes are at least partially complementary to the DNA target material but are different from the first
   type of DNA probes, and attaching double stranded DNA barcodes as identification codes to the surface of the polymer particles wherein the DNA barcodes are present in an amount at least three times the amount of the second type of DNA probes, such that the DNA barcodes have a predetermined sequence portion corresponding to SEQ ID No. 3 and which are labeled with a label material;
   reacting the magnetic particles for isolation, the polymer particles for analysis and the DNA target material in a hybridization reaction buffer to prepare composites, each of which consists of one magnetic particle for isolation, the DNA target material and one polymer particle for analysis;
   separating the composites from unreacted reactants using a magnetic separator;
   heating the separated composites to denature the DNA barcodes present in the polymer particles for analysis and removing the magnetic particles for isolation and the polymer particles for analysis from the composites by centrifugation to isolate the DNA barcodes; and
   detecting a signal generated from the label material bound to the isolated DNA barcodes.

2. The method according to claim 1, wherein the first type of DNA probes have a sequence portion of corresponding to SEQ ID No. 1.

3. The method according to claim 1, wherein the second type of DNA probes are have a sequence portion corresponding to SEQ ID No. 2.

4. The method according to claim 1, wherein the magnetic particles are those having superparamagnetic properties.

5. The method according to claim 4, wherein the superparamagnetic particles are composed of iron-oxide.

6. The method according to claim 1, wherein the magnetic particles have a diameter of 1.0 to 2.8 μm.

7. The method according to claim 1, wherein the polymer particles are composed of a polymeric material of silica.

8. The method according to claim 1, wherein the polymer particles have a diameter of 0.1 to 1.0 μm.

9. The method according to claim 1, wherein the DNA barcodes are double stranded DNAs, each of which consisting of a first type of barcode DNA has a sequence portion corresponding to SEQ ID No. 3 and a second type of barcode DNA has a sequence portion corresponding to SEQ ID No. 4 which is substantially complimentary to the first type of barcode DNA, in which one end of the first type of barcode DNA is labeled with a label material and the other end of the first type of barcode DNA is attached to the surface of the polymer particles; and one end of the second type of barcode DNA is attached to the surface of the polymer particles.

10. The method according to claim 1, wherein the DNA barcodes and the second type of DNA probes are present on the surface of the polymer particles for analysis in a ratio of 3:1 to 1000:1.

11. The method according to claim 1, wherein the heating is conducted at a temperature higher than the melting temperature ($T_m$) of the DNA barcodes to denature the DNA barcodes present in the polymer particles for analysis.

12. The method according to claim 1, wherein the label material is a nanosized magnetic particulate material.

* * * * *